United States Patent
Planas et al.

(10) Patent No.: US 11,666,687 B2
(45) Date of Patent: Jun. 6, 2023

(54) SYSTEMS AND METHODS FOR DETECTING AN EMPTY WB CONTAINER

(71) Applicant: Fenwal, Inc., Lake Zurich, IL (US)

(72) Inventors: Samantha Michalski Planas, Wauconda, IL (US); Melissa A. Thill, Kenosha, WI (US); Ryan Martin, Des Plaines, IL (US)

(73) Assignee: Fenwal, Inc., Lake Zurich, IL (US)

( * ) Notice: Subject to any disclaimer, the term of this patent is extended or adjusted under 35 U.S.C. 154(b) by 389 days.

(21) Appl. No.: 16/883,137

(22) Filed: May 26, 2020

(65) Prior Publication Data

US 2020/0384169 A1    Dec. 10, 2020

Related U.S. Application Data

(60) Provisional application No. 62/857,953, filed on Jun. 6, 2019.

(51) Int. Cl.
*A61M 1/02* (2006.01)
*B01D 63/16* (2006.01)

(52) U.S. Cl.
CPC .......... *A61M 1/024* (2013.01); *A61M 1/0281* (2013.01); *B01D 63/16* (2013.01); *A61M 2202/0415* (2013.01); *A61M 2202/0429* (2013.01); *A61M 2205/3334* (2013.01); *A61M 2205/3393* (2013.01); *A61M 2205/50* (2013.01); *A61M 2205/75* (2013.01)

(58) Field of Classification Search
CPC .. A61M 1/0218; A61M 1/024; A61M 1/0272; A61M 1/0281; A61M 1/262; A61M 2202/0415; A61M 2202/0429; A61M 2205/12; A61M 2205/3334; A61M 2205/3386; A61M 2205/3393; A61M 2205/50; A61M 2205/75; B01D 63/16
See application file for complete search history.

(56) References Cited

U.S. PATENT DOCUMENTS

| | | | |
|---|---|---|---|
| 5,194,145 | A | 3/1993 | Schoendorfer |
| 9,381,291 | B2 | 7/2016 | Boggs et al. |
| 9,649,422 | B2 | 5/2017 | Johnson et al. |
| 9,956,141 | B2 | 5/2018 | Nguyen et al. |
| 2005/0234385 | A1 | 10/2005 | Vandlik et al. |
| 2013/0233394 | A1 | 9/2013 | Nguyen et al. |
| 2018/0243759 | A1 | 8/2018 | Calderon et al. |

OTHER PUBLICATIONS

European Patent Office, Extended European Search Report, counterpart EP Appl. No. 20177808 (dated Nov. 20, 2020) (9 pages).

*Primary Examiner* — Dirk R Bass
(74) *Attorney, Agent, or Firm* — Cook Alex Ltd.

(57) ABSTRACT

A system and method are provided for separating previously-collected whole blood into a red blood cell fraction and a plasma fraction by which the container of previously-collected whole blood is determined to be empty based on using the combination of the measured gross weight of the container and a calculated fluid flow rate from the container, based on weigh scale feedback. Upon detection of the empty container, flow from the container is stopped.

12 Claims, 4 Drawing Sheets

SYSTEMS AND METHODS FOR DETECTING AN EMPTY WB CONTAINER

BACKGROUND

Automated blood processing systems may be used to separate previously-collected whole blood into its constituents, for example into a red blood cell (RBC) product (leukocyte reduced) and a plasma product suitable for use as either fresh frozen plasma or as plasma for further manufacture.

Systems for performing such processes typically include a reusable hardware component and a single use fluid circuit. The hardware component includes pumps, clamps, weigh scales (to measure fluid levels in the containers for the whole blood, RBC, plasma and additive solution), sensors (such as optical and pressure sensors) for assessing whole blood properties, and a programmable controller (including a touch screen for displaying process information and permitting operator input) configured to automatically operate the system. The fluid flow circuits typically include a spinning membrane separator, a cassette module (including interfaces to valves and pressure sensors), a leukocyte reduction filter, and various empty product containers, all interconnected by multiple tubing segments.

In use, a unit of anti-coagulated whole blood (WB) and a container of additive solution are sterile connected to a single-use fluid flow circuit that includes a spinning membrane separator. This may be accomplished by either a separate device or an automated sterile docking system associated with the hardware component. The fluid flow circuit is then installed on the hardware component. The whole blood is separated into red cell concentrate (RCC) and plasma using the spinning membrane separator. The RCC is continuously mixed with additive solution before being pumped through a leukoreduction filter. After separation is completed, the fluid flow circuit is rinsed with additive solution to allow residual RBCs to be recovered and to adjust the volume of additive solution in the container of RBC product to achieve a target volume of additive solution. After separation is completed and the fluid flow circuit has been rinsed with additive solution, the product containers are automatically sealed off from the remainder of the fluid circuit.

In operation, the controller automatically controls the system to prime the fluid flow circuit with additive solution, pump whole blood to the spinning membrane separator, control the spin rate of the spinning membrane, pump red cell concentrate (RCC) out of the spinner (creating passive flow of the plasma), pump additive solution into the RCC, pump the RCC and additive solution through the leukoreduction filter, and flush the set with additive solution at the end of separation. Air is removed from the RBC container and, optionally, the plasma container, and the RBC, plasma and additive solution container lines are sealed.

When processing blood drawn from a container, as contrasted with drawing blood from a donor or patient, care must be taken not to over-empty the container, as over-emptying may result in air entering the fluid circuit. If air enters the separator during separation, the red blood cells may be damaged (i.e., increase in hemolysis), and if air enters the leukoreduction filter, white blood cells (WBCs) may be dislodged into the RBC product (i.e., possible leukoreduction failure). On the other hand, under-emptying the WB container means less RBC and plasma is recovered than was available, and/or may result in the RBC product and plasma product not meeting certain requirements.

By way of the present disclosure, a method and system are described for detecting an empty fluid container, and stopping flow from the container upon such detection.

SUMMARY

In a first aspect, the present disclosure is directed to a system and method for separating previously-collected whole blood into a red blood cell fraction and a plasma fraction by which the container of previously-collected whole blood is determined to be empty by using the combination of the measured gross weight of the container and a calculated fluid flow ate from the container, based on weigh scale feedback. Upon detection of the empty container, flow from the container is stopped.

More specifically, a method is provided for separating previously collected whole blood into at least a first red blood cell fraction and a second plasma fraction using a system comprising a disposable fluid flow circuit comprising a separator and a fluid flow path including a whole blood line connected to a container of whole blood and a durable hardware component comprising a weigh scale, including a hook for supporting the container of whole blood, and a pump for acting on the fluid flow path to control the flow of whole blood from the container of whole blood to the separator. The method comprises: determining a target weight for an empty whole blood container; determining a target flow rate (also referred to as near-empty rate or control rate) of whole blood from the container of whole blood indicative of a near empty whole blood container; flowing whole blood from the container of whole blood to the separator; determining a current weight of the container of whole blood with the weigh scale; calculating a flow rate of whole blood from the container of whole blood; comparing the current weight of the container of whole blood to the target weight for an empty whole blood container and comparing the calculated flow rate of whole blood from the container of whole blood to the target/near-empty/control flow rate of whole blood from the container of whole blood indicative of the near empty whole blood container; and stopping the flow of whole blood from the container of whole blood when both the current weight of the container is equal to or less than the target weight and the calculated flow rate is equal to or less than the target flow rate.

In another aspect, the WB container is determined to be empty based on a measured gross weight of the WB container and a calculated fluid flow rate based on weigh scale feedback, (i.e., based on the rate of change of weight of the WB container). If the net weight of the WB container is sufficiently low (i.e., equal to or less than a predetermined target or control weight), and the flow rate is less than or equal to a predetermined control or target flow rate, the WB container is determined to be empty. The control/target weight utilized by the system for the gross weight of the "empty" container may be entered into the system controller by the operator or pre-programmed into the controller. The predetermined value for the control/target flow rate is sufficiently larger than zero to allow for a known delay between the event, the detection of the event, and when fluid flow stops (i.e., the time it takes for the hardware to change states) to ensure that flow from the container is stopped when the air/blood interface is between the outlet of the WB container and inlet of the WB line into the cassette.

In another aspect, the whole blood pump is operated at a constant pump rate for the WB line that results in a constant WB fluid flow rate when pumping from a "non-empty" WB container. In one embodiment the "non-empty" WB fluid flow rate is 42.75 mL/min. In a first example, the predetermined value for the fluid flow rate when the WB container is "near empty" is 10 mL/min. In a second example, the predetermined value for the fluid flow rate when the WB container is "near empty" is 29 mL/min.

In a further aspect, a system is provided for separating previously-collected whole blood into at least a first red blood cell fraction and a second plasma fraction comprising a durable hardware component and a disposable fluid flow circuit. The disposable fluid flow circuit further comprises a spinning membrane separator, first and second collection containers (for receiving separated RBCs and plasma), a container of additive solution, and a leukocyte reduction filter interconnected by a fluid flow path therebetween, the fluid flow path including a whole blood line configured to be connected to a container of whole blood, and a cassette for controlling fluid flow through the fluid flow circuit. The durable hardware component further comprises: a plurality of pumps one of which is configured for flowing whole blood to the separator, four weigh scales (one for each of the first and second collection containers, the container of additive solution and the container of whole blood), a plurality of clamps/valves; one of which (the WB clamp) is configured to secure and locate the whole blood line relative to the durable hardware component. A programmable controller is provided that is configured to receive operator input, to automatically operate the whole blood pump to control the flow of whole blood from the whole blood container to the separator, to receive signals from the weigh scale for the container of whole blood indicative of a current weight of the container of whole blood, to calculate a flow rate of whole blood from the whole blood container, to compare the current weight of the whole blood container to a control weight to compare the calculated flow rate to a control flow rate, and to control the WB clamp to stop the flow of whole blood from the whole blood container when both the current weight of the whole blood container is equal to or less than the control weight and the calculated flow rate is equal to or less than the control flow rate.

In another aspect, the WB clamp (i.e. the clamp on the reusable hardware component that secures the WB line leading from the WB container to the cassette) is positioned relative to the WB container to minimize potential interference with the WB weigh scale, so that when the controller ends the separation phase based upon the detection of the empty WB container, both the WB container and the WB line between the WB container and the cassettes are clear (i.e., the air/blood interface is between the outlet of the WB container and the inlet of the WB line into the cassette).

DESCRIPTION

A more detailed description of the systems and methods in accordance with the present disclosure is set forth below.

It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
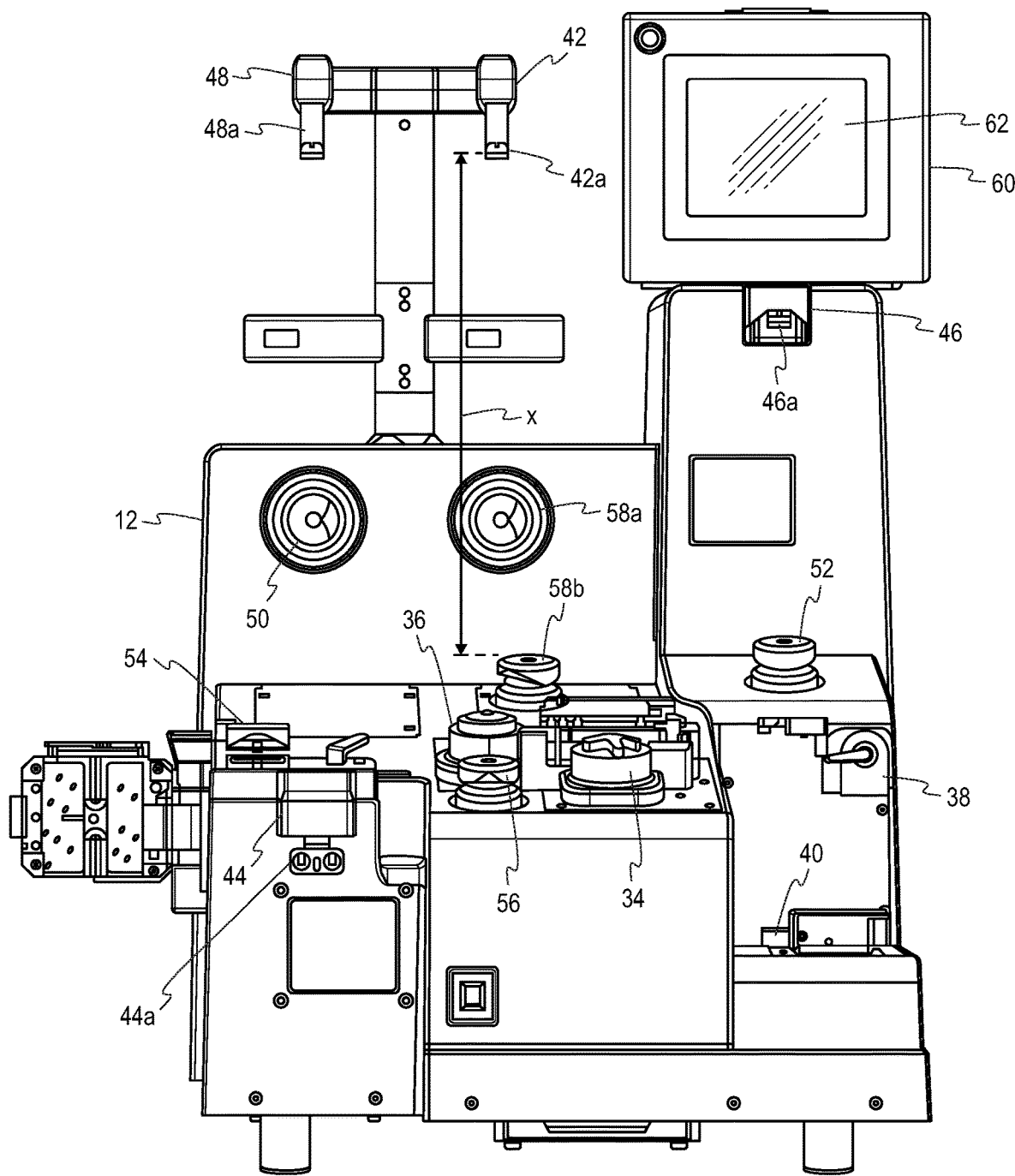
FIG. 1 is a front view of the durable hardware component of a blood processing system in accordance with the present disclosure.
Figure 2:
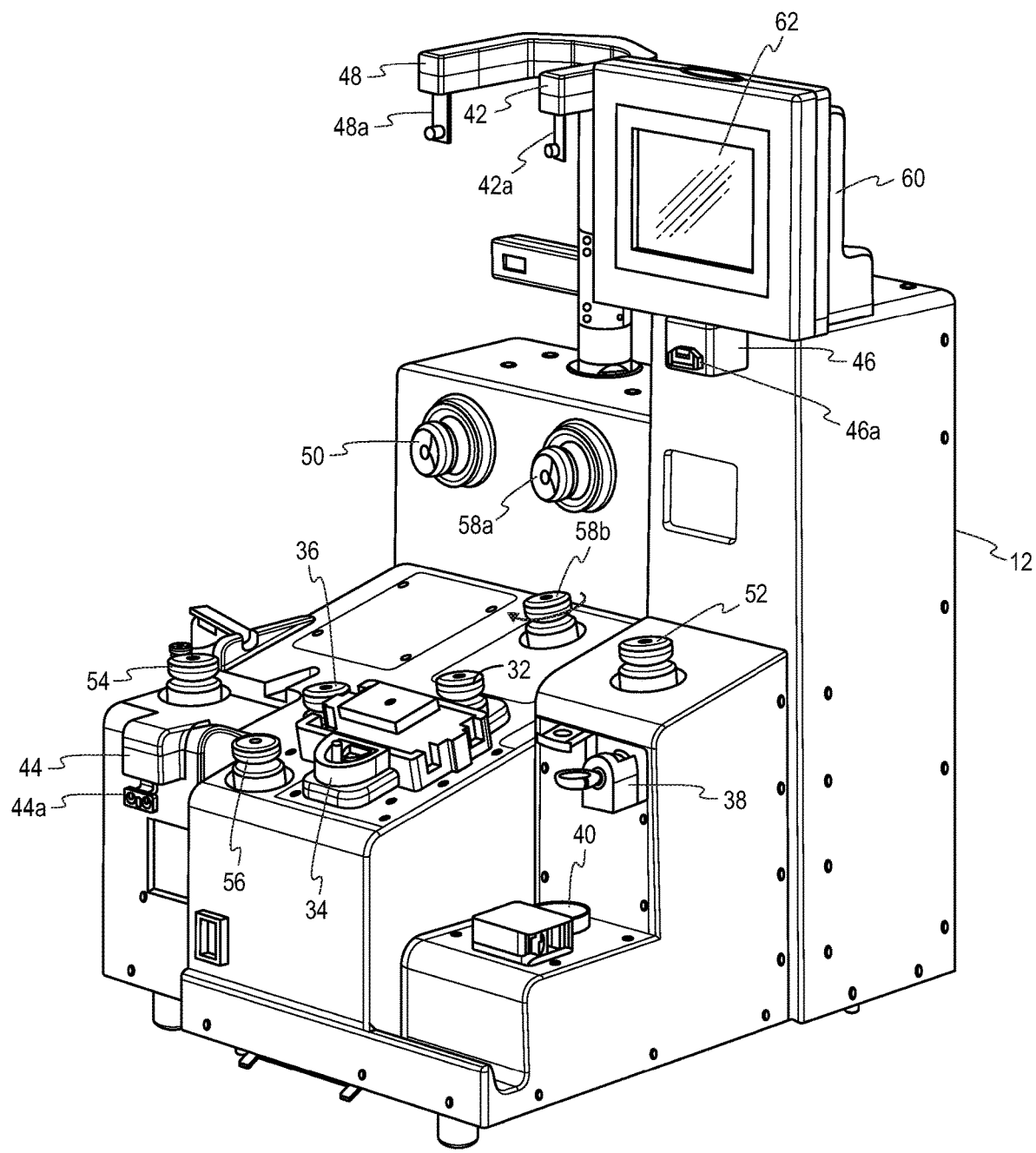
FIG. 2 is a perspective view of the durable hardware component of FIG. 1.
Figure 3:
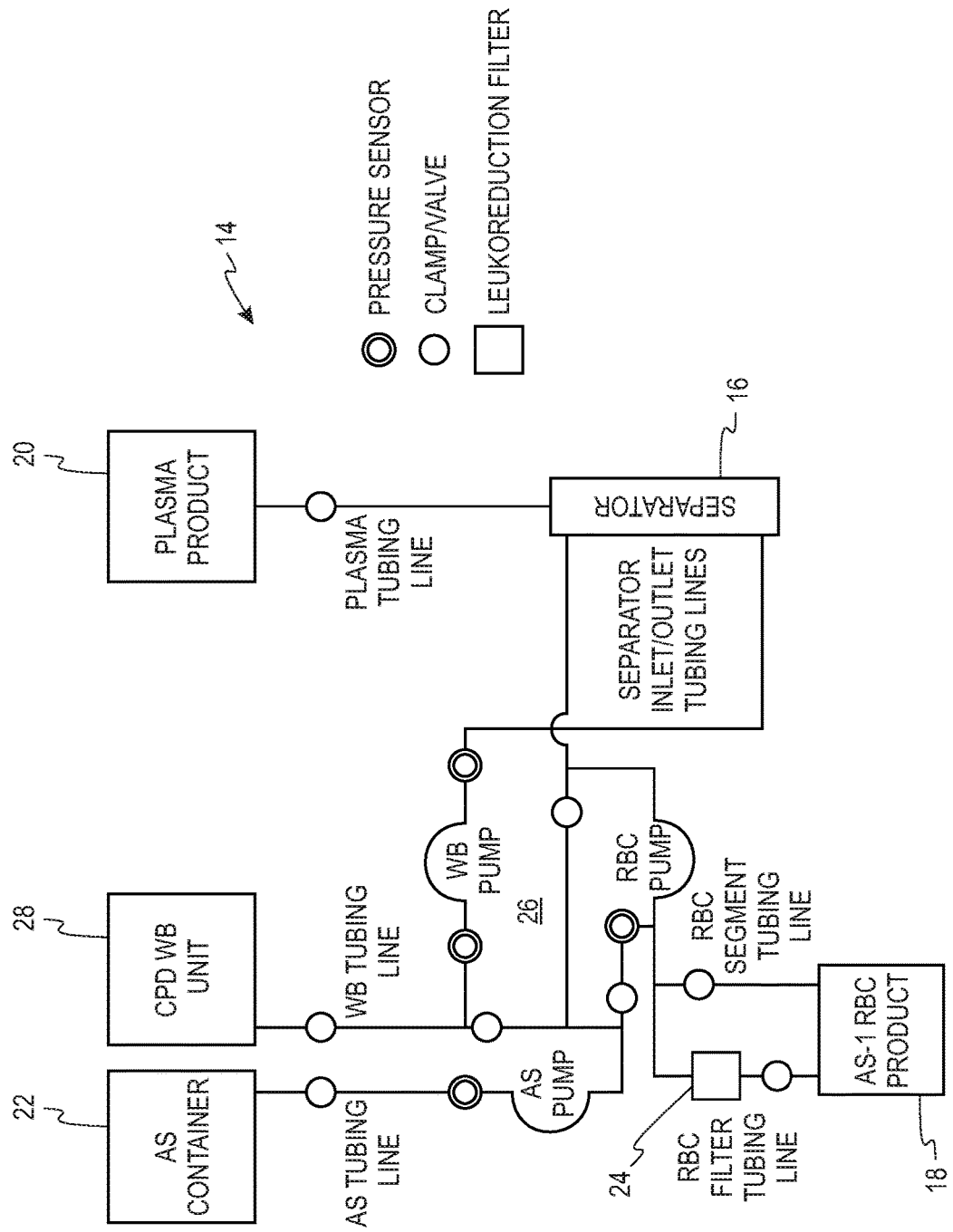
FIG. 3 is a schematic view of the disposable fluid flow circuit of a blood processing system in accordance with the present disclosure for use in combination with the durable hardware component of FIGS. 1 and 2.

Turning to the drawings, FIGS. 1 and 2 depict the durable hardware component 12 and FIG. 3 depicts the disposable fluid flow circuit 14 that together comprise a blood processing system in accordance with the present disclosure. The blood processing system is a post-collection blood processing system for processing previously collected whole blood. A representative system is shown and described in US 2018/0243759, which is incorporated herein by reference in its entirety.

The durable hardware component 12 includes associated pumps, clamps, weigh scales, sensors, displays and other apparatus for configuring and controlling flow of blood and additive solution (also referred to as AS) through the fluid flow circuit 14. The blood processing system is directed by an internal controller that includes a programmable microprocessor that automatically controls the operation of the system.

The fluid flow circuit comprises a spinning membrane separator 16, pre-attached collection containers 18, 20 for receipt of separated RBCs and plasma, respectively, a container 22 of additive solution, a leukocyte reduction filter 24, and various tubing segments that interconnect the containers. A detailed description of a spinning membrane separator may be found in U.S. Pat. No. 5,194,145 to Schoendorfer, and in U.S. Pat. No. 9,381,291 to Boggs et al., both of which are incorporated by reference herein. A pump cassette 26 routes the fluid flow through the circuit by means of three tubing loops that extend from the cassette to engage one of the pumps associated with the durable hardware component 12. A container 28 of whole blood is attached to the fluid flow circuit at the time of use. The container 22 of additive solution may be pre-attached to the fluid flow circuit, or also be attached at the time of use. As noted above, containers 28 and 22 may be manually attached to the fluid circuit, but are preferably attached to the fluid circuit by means of an automated sterile docking system incorporated into the hardware component.

The durable hardware component 12 includes a front panel to which the cassette 26 is mounted so that the tubing loops are in engagement with a whole blood pump 32, a RBC pump 34, and an additive solution pump 36. The spinning membrane separator 16 is mounted to the durable hardware component by means of upper support arm 38 and lower support cup 40, the latter including a magnetic drive system for rotating the membrane of the separator 16. Each of the whole blood container 28, RBC container 18, plasma container 20 and additive solution container 22 is supported on a weigh scale, namely whole blood scale 42, RBC scale 44, plasma scale 46, and additive solution scale 48, respectively. Each scale 42, 44, 46 and 48 comprises a hook 42a, 44a, 46a and 48a for supporting their respective containers.

The durable hardware component further comprises a plurality of clamps/valves on the front panel for locating and securing the various tubing segments in their desired location and for controlling the direction of fluid flow through the circuit. The clamps include an additive solution clamp 50, a plasma clamp 52, a RBC clamp 54, a segment clamp 56, and a whole blood clamp 58a or 58b. Both clamps 58a and 58b are shown in FIGS. 2 and 3, with clamp 58a being on a vertical portion of the front panel and clamp 58b being on a horizontal portion of the front panel. However, the durable hardware component includes only a single whole blood clamp. As set forth in greater detail below, whole blood clamp 58b is preferred.

The durable hardware component 12 also includes a programmable controller 60 that includes a touch screen 62 to permit operator input and to also display information regarding the blood processing procedure. The controller 60 receives signals from the weigh scales and other sensors, and automatically controls the system to prime the fluid flow circuit with additive solution, pump whole blood to the spinning membrane separator, control the spin rate of the spinning membrane, pump red cell concentrate (RCC) out of the spinner (creating passive flow of the plasma), pump additive solution into the concentrated RCC, pump the RCC and additive solution through the leukoreduction filter, and flush the set with additive solution at the end of separation.

As noted above, when processing blood drawn from a container, care must be taken not to over-empty the container, as over-emptying may result in air entering the separator (leading to RBC hemolysis) and/or leukoreduction filter (leading to a leukoreduction failure). On the other hand, under-emptying the WB container means lower RBC recovered and less plasma is collected than was available, which may lead to not meeting various collection requirements.

Accordingly, in keeping with the present disclosure, the container of previously-collected whole blood 28 is determined to be empty based on using the combination of the measured gross weight of the container 28 and a calculated fluid flow rate from the container, based on weigh scale feedback. Upon detection of the empty container, flow from the container is stopped.

More specifically, the WB container 28 is determined to be empty based on a measured gross weight of the WB container and a calculated fluid flow rate based on weigh scale feedback, i.e., based on the rate of change of weight of the WB container 28. If the net weight of the WB container 28 is sufficiently low, and the flow rate is less than a predetermined target flow rate, the WB container 28 is considered to be empty, and the processor will stop the flow from the WB container by, e.g., closing the WB clamp 58a/58b or stopping the WB pump 32.

The value for the measured gross weight of the "near empty" container may be entered into the system controller by the operator or pre-programmed into the controller, while the predetermined value for the target flow rate is sufficiently larger than zero to allow for a known delay between the event, the detection of the invent and the time it takes for the hardware component to change states, to ensure that flow from the container is stopped when the air/blood interface is between the outlet of the WB container 28 and inlet of the WB line into the cassette 26.

Further, the WB pump 32 is operated at a constant pump rate for the WB line. This results in a constant WB fluid flow rate when pumping from a "non-empty" WB container. In one embodiment the "non-empty" WB fluid flow rate is 42.75 mL/min. In a first example, the predetermined value for the fluid flow rate when the WB container 28 is "near empty" is 10 mL/min. In a second example, the predetermined value for the fluid flow rate when the WB container 28 is "near empty" is 29 mL/min.

Figure 4:
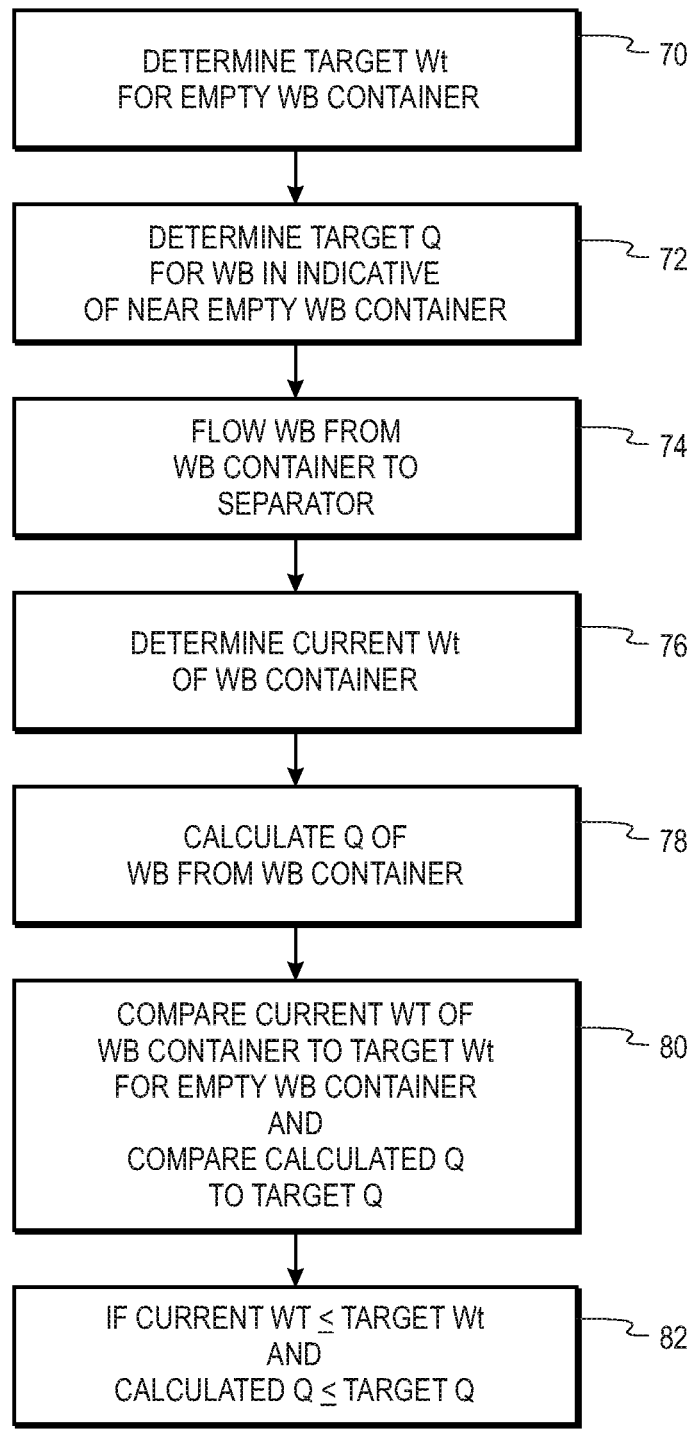
FIG. 4 is a flow chart illustrating the steps of the method for detecting an empty container in accordance with the present disclosure.

With reference to FIG. 4, a flow chart is provided that illustrates the steps of the method. First, a target/control weight is established for the empty whole blood container (Box 70). Then, a target/control flow rate (Q) is established for the whole blood from the container that is indicative of a near empty whole blood container (Box 72). The separation of the whole blood is then commenced by flowing whole blood from the whole blood container to the separator (Box 74). During the separation of the whole blood, the current weight of the whole blood container is measured/monitored (Box 76) and the flow rate of whole blood from the whole blood container calculated (Box 78), by, e.g., the controller. The current weight of the whole blood container is compared to the target/control weight for an empty whole blood container and the calculated flow rate of whole blood form the container of whole blood is compared to the target/control flow rate of whole blood from the container of whole blood that is indicative of the near empty whole blood container (Box 80), again by, e.g., the controller. If both the current weight of the container of whole blood is equal to or less than the target weight and the calculated flow rate is equal to or less than the target flow rate, flow from the whole blood container is stopped (Box 82).

A problem with determining whether the whole blood container is empty based upon a weigh scale measurement is that the manner in which the tubing from the whole blood container is clamped to the durable hardware component can interfere with the accuracy of the weigh scale. There should be a sufficient amount of slack in the whole blood tubing between the whole blood container and the whole blood clamp to ensure that there the tubing does not affect the weight measured by the weigh scale and/or cause the tubing to kink where it is engaged by the clamp.

It has been determined that if the whole blood clamp is located on the vertical portion of the front panel, as is clamp 58a, where the damp 58a is in relatively close proximity to the hook of the weigh scale, significant scale interference is more likely than when the whole blood clamp is located on the horizontal portion of the front panel, as is clamp 58b. By increasing the distance between the clamp and the weigh scale hook, the criticality of proper loading of the fluid flow circuit onto the hardware component to avoid scale interference is reduced. In one embodiment, a vertical distance X (as seen in FIG. 1) of approximately 15.8" between the whole blood weigh scale hook 42a and the clamping point of the clamp 58b was found to satisfactorily ameliorate interference of the whole blood clamp with the whole blood weigh scale.

In addition, the location on the clamp that engages the tubing segment can also affect weigh scale interference. Specifically, rotation of the clamp 58b to where the clamping point is approximately at 7:30 o'clock relative to the front panel (as seen in FIG. 2) was found to further reduce clamp interference with the weigh scale 42.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein.

We claim:

1. A method for separating previously collected whole blood into at least a first red blood cell fraction and a second plasma fraction using a system comprising a disposable fluid flow circuit comprising a separator and a fluid flow path including a whole blood line connected to a container of whole blood and a durable hardware component comprising a weigh scale for the container of whole blood and a pump for acting on the fluid flow path to control the flow of whole blood from the container of whole blood to the separator, the method comprising:

a) determining a target weight for an empty whole blood container;
b) determining a target flow rate of whole blood from the container of whole blood indicative of a near empty whole blood container;
c) flowing whole blood from the container of whole blood to the separator;
d) determining a current weight of the container of whole blood with the weigh scale;
e) calculating a flow rate of whole blood from the container of whole blood;
f) comparing the current weight of the container of whole blood to the target weight for an empty whole blood container and comparing the calculated flow rate of whole blood from the container of whole blood to the target flow rate of whole blood from the container of whole blood indicative of the near empty whole blood container; and
g) stopping the flow of whole blood from the container of whole blood when both the current weight is equal to or less than the target weight and the calculated flow rate is equal to or less than the target flow rate.

2. The method of claim 1 in which the fluid flow rate is calculated based on a rate of change of weight of the whole blood container of claim 1.

3. The method of claim 1 wherein the target flow rate is greater than zero.

4. The method of claim 3 wherein the target flow rate is 10 mL/min.

5. The method of claim 3 wherein the target flow rate is 29 mL/min.

6. A system for separating previously-collected whole blood into at least a first red blood cell fraction and a second plasma fraction comprising a durable hardware component and a disposable fluid flow circuit:
a) the disposable fluid flow circuit further comprising: a separator (preferably a spinning membrane separator); first and second collection containers; a container of additive solution; and a leukocyte reduction filter interconnected by a fluid flow path therebetween, the fluid flow path including a whole blood line configured to be connected to a container of whole blood, and a cassette for controlling fluid flow through the fluid flow circuit;
b) the durable hardware component further comprising: a plurality of pumps, one of which is configured for flowing whole blood to the separator; a weigh scale for each of the first and second collection containers, the container of additive solution and the container of whole blood; a plurality of clamps, one of which is configured to secure and locate the whole blood line relative to the durable hardware component; and a programmable controller configured to receive operator input, to automatically operate the whole blood pump to control the flow of whole blood from the whole blood container to the separator, to receive signals from the weigh scale for the container of whole blood indicative of a current weight of the container of whole blood, to calculate a flow rate of whole blood from the whole blood container, to compare the current weight of the whole blood container to a control weight and to compare the calculated flow rate to a control flow rate, and to stop the flow of whole blood from the whole blood container when both the current weight of the whole blood container is equal to or less than the control weight and the calculated flow rate is equal to or less than the control flow rate.

7. The system of claim 6 in which the control weight is pre-programmed into the controller.

8. The system of claim 6 in which the control flow rate is pre-programmed into the controller.

9. The system of claim 6 in which the controller is configured to calculate the fluid flow rate based on a rate of change of weight of the whole blood container.

10. The system of claim 6 wherein the control flow rate is greater than zero.

11. The system of claim 6 wherein the durable hardware component further comprises a hook for supporting the container of whole blood and the clamp configured to secure and locate the whole blood line relative to the durable hardware component is spaced from the hook a distance sufficient to reduce scale interference.

12. The system of claim 11 wherein the clamp configured to secure and locate the whole blood line relative to the durable hardware component is spaced from the hook a distance of 15.8".

* * * * *